(12) United States Patent
Monat et al.

(10) Patent No.: US 10,292,857 B2
(45) Date of Patent: May 21, 2019

(54) HEAD-AND-NECK IMMOBILIZATION DEVICES AND RELATED METHODS

(71) Applicant: Cornerstone Research Group, Inc., Dayton, OH (US)

(72) Inventors: Jacob A. Monat, Yellow Springs, OH (US); Joseph H. Althaus, Yellow Springs, OH (US); Matthew B. Sunday, California, KY (US); Jason M. Hermiller, Lebanon, OH (US); Kelly H. Ridout, New Paris, OH (US); Kristin M. Cable, Dayton, OH (US)

(73) Assignee: Cornerstone Research Group, Inc, Dayton, OH (US)

( * ) Notice: Subject to any disclaimer, the term of this patent is extended or adjusted under 35 U.S.C. 154(b) by 545 days.

(21) Appl. No.: 14/827,131

(22) Filed: Aug. 14, 2015

(65) Prior Publication Data

US 2017/0042719 A1    Feb. 16, 2017

(51) Int. Cl.
*A61F 5/055* (2006.01)
*A61F 5/058* (2006.01)

(52) U.S. Cl.
CPC .......... *A61F 5/055* (2013.01); *A61F 5/05883* (2013.01)

(58) Field of Classification Search
CPC .. A61F 5/055; A61F 5/05; A61F 5/042; A61F 5/048; A61F 5/05883; A61F 5/05891; A61F 5/058; A61F 5/37; A61F 5/3707; A61F 2005/0151; A61F 2005/0169; A42B 3/0473; A61H 1/0296; A61H 1/0292; A61H 2201/1604; A61H 2201/1607;

(Continued)

(56) References Cited

U.S. PATENT DOCUMENTS 3,957,040 A    5/1976    Calabrese
4,593,788 A    6/1986    Miller (Continued)

FOREIGN PATENT DOCUMENTS

CA    2002800        11/1992
EP    0023115 B1    11/1985
WO    2010070340 A1    6/2010

OTHER PUBLICATIONS

Brain, M. (Jul. 27, 2009). How much does the human head actually weigh? Retrieved Nov. 21, 2017, from https://www.brainstuffshow.com/blogs/how-much-does-the-human-head-actually-weigh.htm.*

(Continued)

*Primary Examiner* — Alireza Nia
*Assistant Examiner* — Rachel A Berezik
(74) *Attorney, Agent, or Firm* — TraskBritt (57) ABSTRACT

Head-and-neck immobilization devices may include a yoke sized and shaped to contact a person's back and shoulders. Straps may extend from the yoke, the straps configured to secure the yoke to the person's torso. Two head immobilization pads may be sized and shaped to respectively contact opposing sides of the person's head, each of the two head immobilization pads connected to the yoke by a respective selectively rotatable, selectively rigid connection. A majority of the person's head may remain unobstructed by the head-and-neck immobilization device when the two head immobilization pads contact the two opposing sides of the person's head and are rigidly secured in place to immobilize the person's neck and head.

17 Claims, 9 Drawing Sheets

(58) Field of Classification Search
CPC .. A61G 13/12; A61G 13/1205; A61G 13/121; A61G 13/1215; A61G 1/04; A61G 5/121; A63B 71/1291
See application file for complete search history.

(56) References Cited

U.S. PATENT DOCUMENTS

| | | | |
|---|---|---|---|
| 4,899,736 | A | 2/1990 | Nesbitt |
| 5,242,377 | A | 9/1993 | Boughner et al. |
| 6,435,188 | B2 | 8/2002 | Tyrrell |
| 6,447,468 | B1 | 9/2002 | Hankins et al. |
| 6,968,576 | B2 | 11/2005 | McNeil et al. |
| 7,371,221 | B1 | 5/2008 | Baker |
| 8,057,415 | B2 * | 11/2011 | Hipp ................. A61F 5/055 2/410 |
| 8,834,394 | B2 * | 9/2014 | Ghajar ............... A61F 5/055 128/846 |
| 2003/0088906 | A1 * | 5/2003 | Baker ................ A42B 3/0473 2/416 |
| 2006/0137097 | A1 | 6/2006 | Frost |
| 2009/0187129 | A1 | 7/2009 | Ben-Galim et al. |
| 2010/0298748 | A1 * | 11/2010 | Rosenfeld ........... A61F 5/055 602/17 |
| 2011/0009789 | A1 | 1/2011 | Barns |
| 2011/0060260 | A1 * | 3/2011 | Siegler ............... A42B 3/0473 602/18 |
| 2011/0240042 | A1 | 10/2011 | Cooke et al. |

OTHER PUBLICATIONS

Brain, M. (Jul. 27, 2009). How much does the human head actually weigh? Retrieved Apr. 26, 2018, from https://www.brainstuffshow.com/blogs/how-much-does-the-human-head-actually-weigh.htm.*

* cited by examiner

HEAD-AND-NECK IMMOBILIZATION DEVICES AND RELATED METHODS

STATEMENT REGARDING FEDERALLY SPONSORED RESEARCH OR DEVELOPMENT

This invention was made with U.S. Government support under Contract Number. W81XWH-10-C-0193 awarded by U.S. Army Medical Research Acquisition Activity (USAMRAA) to Cornerstone Research Group Inc. The U.S. Government has certain rights in the invention.

FIELD

This disclosure relates generally to head-and-neck immobilization devices to support and substantially immobilize the head and neck of a person. More specifically, disclosed embodiments relate to head-and-neck immobilization devices that may be easier to place on an injured person, may adjust to fit a greater variety of people, and may reduce contact area with a person's body while providing support to the person's head and neck.

BACKGROUND

When a person suffers a head or spinal injury, their head and neck may be immobilized to reduce the risk of further injury during transport and treatment. For example, neck braces, backboards, and crown-encircling stabilizers (also known in the art as "halo" devices) may be used conventionally to support a person's head and neck to reduce the risk of further injury.

People that experience traumatic injuries must endure a great deal of handling and movement by, for example, search and rescue and medical personnel during transport from an injury site to medical facilities with definitive treatment capabilities. This transport often involves both ground transport and flight on rotary and/or fixed-wing aircraft. Proper immobilization and shock load isolation may reduce the mortality and comorbidities associated with these casualties while in transit. Equipment currently used for people with a spinal cord injury (SCI) or traumatic brain injury (TBI) may provide some level of immobilization. However, such equipment may not be effective to isolate the patient from the dynamic multi-axial shock loading and vibrations present during transport. Treatment efficacy may be further diminished due to the current systems' inability to properly address polytrauma treatment issues, provide clear access to injury sites, manage bodily fluids, reduce the risk of pressure ulcerations, or be applied to an injured person in a variety of positions and orientations. With the increasing prevalence of SCI, TBI, and polytrauma patients due to the expanded use of improvised explosive devices (IED) on military forces, a renewed transport platform design may improve the specific transport, safety, care, and comfort needs of both the injured and caregivers.

BRIEF SUMMARY

In some embodiments, head-and-neck immobilization devices may include a yoke sized and shaped to contact a person's back and shoulders. Straps may extend from the yoke, the straps located and configured to secure the yoke to the person's torso. Two head immobilization pads may be sized and shaped to respectively contact opposing sides of the person's head, each of the two head immobilization pads connected to the yoke by a respective selectively rotatable, selectively rigid connection. A majority of the person's head may remain unobstructed by the head-and-neck immobilization device when the two head immobilization pads contact the two opposing sides of the person's head and are rigidly secured in place to immobilize the person's neck and head.

In other embodiments, methods of making head-and-neck immobilization devices may involve sizing and shaping a yoke sized to contact a person's back and shoulders. Straps may be secured to the yoke such that the straps extend from the yoke, the straps located and configured to secure the yoke to the person's torso. Each of two head immobilization pads may be connected to the yoke by a selectively rotatable, selectively rigid connection, the two head immobilization pads being sized and shaped to respectively contact opposing sides of the person's head. Each of the two head immobilization pads and each selectively rotatable, selectively rigid connection may be configured such that a majority of the person's head remains unobstructed by the head-and-neck immobilization device when the two head immobilization pads contact the two opposing sides of the person's head and are rigidly secured in place to immobilize the person's neck and head.

In still other embodiments, methods of using head-and-neck immobilization devices may involve contacting a yoke to a person's back and shoulders. Straps extending from the yoke may be secured around the person's torso to secure the yoke to the person's torso. Two head immobilization pads may be respectively contacted to opposing sides of the person's head, each of the two head immobilization pads connected to the yoke by a selectively rotatable, selectively rigid connection, and the selectively rotatable, selectively rigid connection may be rendered rigid to immobilize the person's head and neck. A majority of the person's head may be left unobstructed by the head-and-neck immobilization device when the two head immobilization pads contact the two opposing sides of the person's head and are rigidly secured in place to immobilize the person's neck and head.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

The illustrations presented in this disclosure are not meant to be actual views of any particular apparatus or component thereof, but are merely idealized representations employed to describe illustrative embodiments. Thus, the drawings are not necessarily to scale.

Disclosed embodiments relate generally to head-and-neck immobilization devices that, in comparison to conventional devices, may be easier to place on a person, may be adjusted to fit individuals of a greater variety of shapes and dimensions, may reduce contact area with a person's body, and may reduce the use of invasive procedures for securing the device onto the person while providing support to immobilize the person's head and neck.

Figure 1:
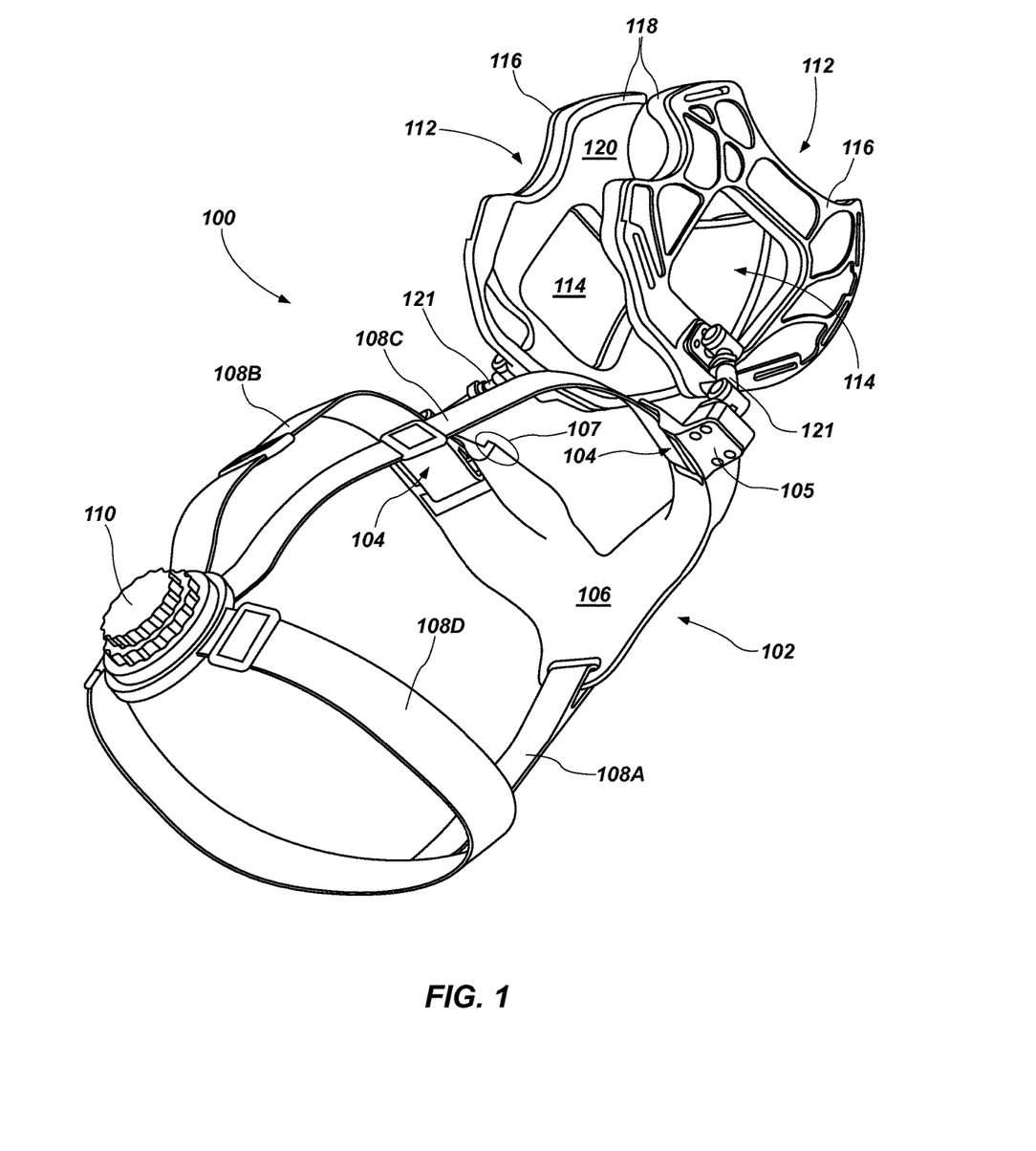
FIG. 1 is a perspective view of a head-and-neck immobilization device.

Referring to FIG. 1, a perspective view of an embodiment of a head-and-neck immobilization device 100 of the present disclosure is shown. The head-and-neck immobilization device 100 may include a yoke 102 sized and shaped to contact a person's upper back and shoulders. The yoke 102 may include shoulder portions 104 sized, positioned, shaped, and oriented to contact respective shoulders of the person. The shoulder portions 104 may comprise, for example, curved sections of material at opposing lateral sides of the yoke 102. A slope of the shoulder portions 104 may be at least substantially zero proximate a coronal plane of the person's body (i.e., a plane dividing the person's body into ventral and dorsal, also known as belly and back, sections). The yoke 102 may include an upper back portion 106 sized, positioned, shaped, and oriented to contact the upper back of the person. The upper back portion 106 may have a V- or Y-shape open profile to reduce contact area with the person's body, reducing pressure sores and increasing access to person's cervical spine (i.e., the upper spine section). In some embodiments, the yoke include an overall neck width space of approximately 7.7 in from left to right to accommodate persons with wide necks. The upper back portion 106 may comprise another curved section of material oriented substantially perpendicular to the shoulder portions 104, extending between the shoulder portions 104, and connecting the shoulder portions 104 to one another. The yoke 102 may have a substantially uniform thickness of about 0.2 in to provide sufficient material for load transfer while reducing size, weight, and thickness which could result in discomfort or pressure sores. The yoke 102 may also have increased thickness of approximately 0.4 in in some or all areas, such as, for example, on the outside of the shoulder portions 104, where it interfaces with the head block adjustment mechanisms, to provide sufficient load transfer of head loads subject to crash, impact, or acceleration event. The yoke 102 may include at least two mounting pads 105 exhibiting thicknesses of about 0.5 in to about 1.0 in on each of the shoulder portions 104 for interfacing with a head block adjustment mechanism. In some embodiments, the mounting pads 105 may include mounting holes for interfacing with the head block adjustment mechanism using, for example, bolts, screws, or pins. As a specific example, each mounting pad 105 may include four mounting holes for interfacing with the head block adjustment mechanism. In some embodiments, the yoke 102 may include at least two raised edges 107 located over the shoulder portions 104 to reduce the likelihood that straps employed to strap the person to a litter platform will interfere with the person's neck or slide off the person's shoulder. In some embodiments, the yoke 102 may include multiple openings for looped strap connection points. As a specific non-limiting example, the yoke may include three openings, one on each shoulder and one on back, for looped strap connection. A material of the yoke 102 may be, for example, rigid, strong, and lightweight to impart stability and portability to the head-and-neck immobilization device 100. More specifically, the material of the yoke 102 may be, for example, a polymer material or a composite material. As specific, nonlimiting examples, the material of the yoke 102 may be, for example, fiberglass or carbon fiber composite material (e.g., carbon fibers in a nylon resin matrix). In some embodiments, a cushioning material, such as, for example, closed-cell, medical-grade foam, may line all or a portion of a person-facing side of the yoke 102.

Straps 108 extending from the yoke 102 may be configured to secure the yoke 102 to the person's torso. The straps 108 may include, for example, a first strap 108A extending from the upper back portion 106 of the yoke 102. The first strap 108A may extend longitudinally from a laterally central location on the upper back portion 106 of the yoke 102, along the person's spine, toward the person's waist. A second strap 108B and a third strap 108C may extend longitudinally from respective shoulder portions 104 of the yoke 102, along the person's chest, toward the person's waist. A fourth strap 108D may extend laterally from a bottom of the first strap 108A, around the person's torso, toward the person's sternum or navel. Distal ends of the second, third, and fourth straps 108B, 108C, and 108D may converge at, and be releasably securable to, a buckle 110 at a proximal end of the fourth strap 108D. When the second, third, and fourth straps 108B, 108C, and 108D are secured to the buckle 110, the yoke 102 may be securely fastened to the person's torso. The straps 108 may be adjustable in length to accommodate people of varying sizes. The straps 108 may be formed of, for example, a medical-grade polymer material. Although one specific configuration for a set of straps 108 is shown and described in connection with FIG. 1, many other suitable configurations of straps for securing the yoke 102 to the person's torso may be used.

The head-and-neck immobilization device 100 may include two head immobilization pads 112, each pad 112 sized and shaped to contact two opposing sides of the person's head. The head immobilization pads 112 may be curved to at least substantially conform to a shape of a person's head. The head immobilization pads 112 may include access holes 114 extending through the head immobilization pads 112, which may grant others access to exposed portions of the person's head and may reduce the risk of pressure ulcerations. The access holes 114 may leave, for example, the person's ears, portions of the person's head immediately surrounding the ears, and other portions of the person's head further from the ears but still within the footprint of the immobilization pads 112 exposed. In some embodiments, a majority of an area of each of the head immobilization pads 112 within a periphery of each of the head immobilization pads 112 may be occupied by the access holes 114. The head immobilization pads 112 may be sized and shaped to conform to adult male heads from the 5th to the 95th percentile in terms of size and shape. Of course, smaller, female-sized and pediatric-sized versions of the head-and-neck immobilization device of embodiments of the disclosure may be easily fabricated.

The head immobilization pads 112 may each include an outer shell 116 located distal from the person's head and an inner padding 118 located proximal to the person's head. A material of the outer shell 116 may be, for example, a rigid, strong material to impart stability and strength to the head immobilization pads 112. More specifically, the material of the outer shell 116 may be, for example, a polymer material or a composite material. As specific, nonlimiting examples, the material of the outer shell 116 may be, for example, fiberglass or carbon fiber composite material (e.g., carbon fibers in a nylon resin matrix). A material of the inner padding 118 may be, for example, a closed-cell medical grade foam. In some embodiments, outer surfaces of the inner padding 118 may comprise a coating 120, selected, for example, to enable easier cleaning or improve comfort of the person wearing the head-and-neck immobilization device 100.

Each of the two head immobilization pads 112 may be connected to the yoke 102 by a respective selectively rotatable, selectively rigid connection 121. The selectively rotatable, selectively rigid connections 121 may enable the head immobilization pads 112 to move laterally when desired to position the head immobilization pads 112 closer to or farther away from the person's head and to remain stationary when desired to stabilize the person's head and neck. Materials of the selectively rotatable, selectively rigid connections 121 may be, for example, rigid, strong materials to enable the selectively rotatable, selectively rigid connections 121 to immobilize the person's head and neck. More specifically, the materials of the selectively rotatable, selectively rigid connections 121 may be, for example, a metal or composite material. As specific, nonlimiting examples, the materials of the selectively rotatable, selectively rigid connections 121 may be steel (e.g., stainless steel), aluminum, or carbon fiber reinforced polymer composite.

Figure 2:
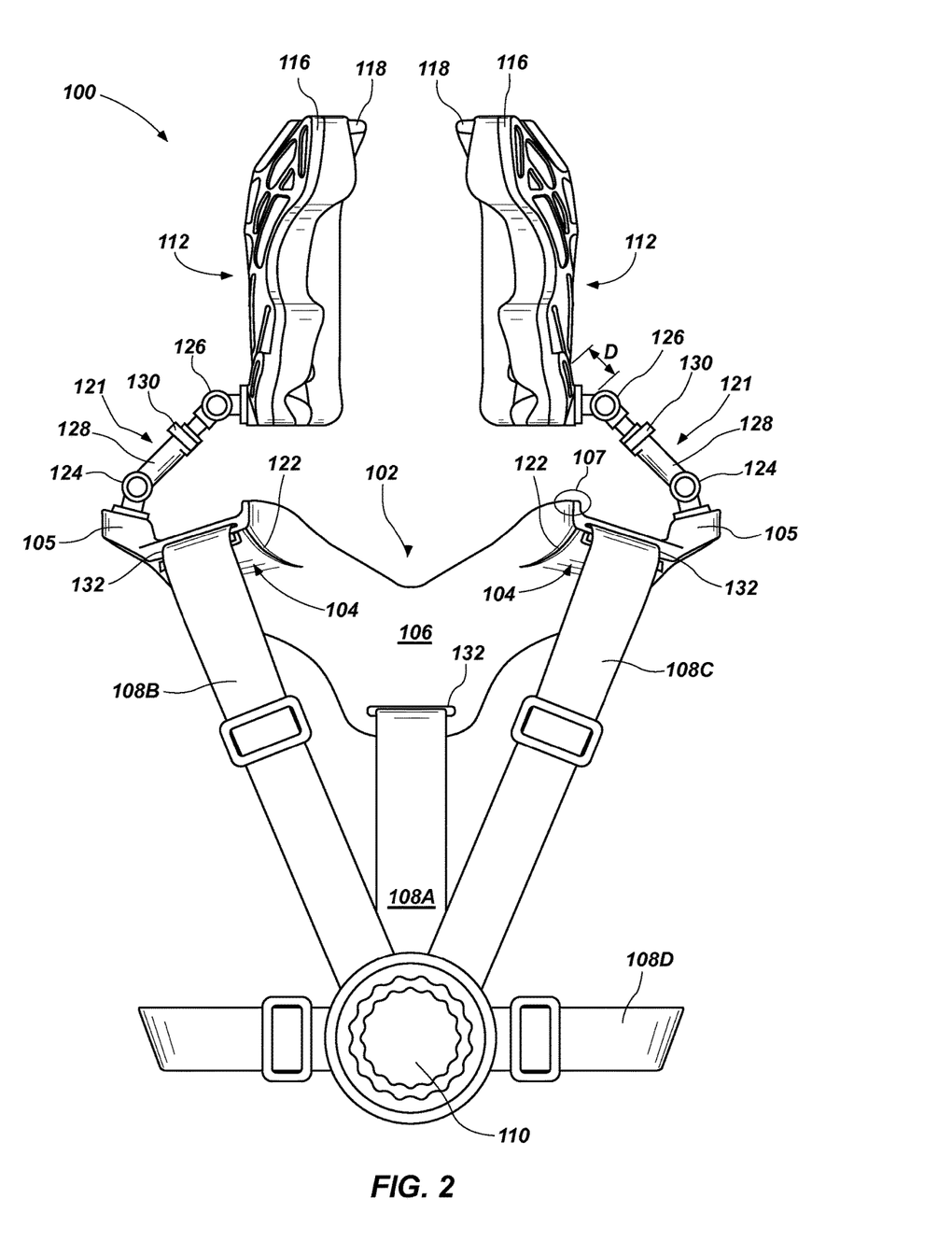
FIG. 2 is a front view of the head-and-neck immobilization device of FIG. 1.

FIG. 2 is a front view of the head-and-neck immobilization device 100 of FIG. 1. The selectively rotatable, selectively rigid connections 121 may include multiple points of articulation, such as, for example, by being rotatable about at least two axes of rotation, to increase the adjustability of the head immobilization pads 112. For example, the selectively rotatable, selectively rigid connections 121 may include a first hinge 124 located adjacent to the yoke 102 and a second hinge 126 located adjacent to the respective head immobilization pad 112. The first and second hinges 124 and 126 may be configured to rotate independently when in a first state and to remain fixed when in a second state. For example, the first and second hinges 124 and 126 may be independently, releasably lockable to enable rotation and movement when desired and fixation when desired. As specific, nonlimiting examples, the first and second hinges 124 and 126 may be VARILOC® hinges, offered by Adjustable Locking Technologies of Bloomfield Hills, Mich., or an Arca-Swiss-style ballhead having a screw clamp receiver permitting multi-axial rotation.

The first and second hinges 124 and 126 may be spaced from one another by a spacer 128. The spacer 128 may comprise, for example, a rod or bar connecting the first and second hinges 124 and 126 to one another. In some embodiments, the spacer 128 may be selectively longitudinally extendable, rendering the selectively rotatable, selectively rigid connections 121 extensible to enable a broader range of adjustability for the head immobilization pads 112. For example, the spacer 128 may include a first portion located within, and slidable relative to, another portion of the spacer 128 in a telescoping manner, and a locking mechanism 130 (e.g., a quick-release cuff or a cam locking device including a pivoted constant rise cam member having a lever handle, a release section, and a locking section operable by compressing or impinging two surfaces together to effect the locking, and releasing such compressing or impinging state for unlocking) to secure the spacer 128 in place when at a desired length. A telescoping distance of the spacer 128 (i.e., a maximum extensible displacement of the head immobilization pads 112) may be, for example, at least about 1 in. More specifically, the telescoping distance of the spacer 128 may be, for example, at least about 2 in. As specific, nonlimiting examples, the telescoping distance of the spacer may be, for example, at least about 3 in, at least about 4 in, or more. In other embodiments, the spacer 128 may not be extendable.

In some embodiments, the yoke 102 may include shoulder pads 122 located on the shoulder portions 104 of the yoke 102 to increase comfort of the person wearing the head-and-neck immobilization device 100. The shoulder pads 122 may comprise, for example, of a closed-cell, medical-grade foam.

The first, second, and third straps 108A, 108B, and 108C may be secured to the yoke 102 by yoke attachment structures 132. The yoke attachment structures 132 may include, for example, slots, holes, hooks, hook-and-pile attachments, or other structures for securing a band of material (e.g., webbing) to the yoke 102. In some embodiments, the yoke 102 may include additional yoke attachment structures 132 to enable repositioning of the straps 108 or to enable securing the yoke 102 to a backboard by another strap.

Figure 3:
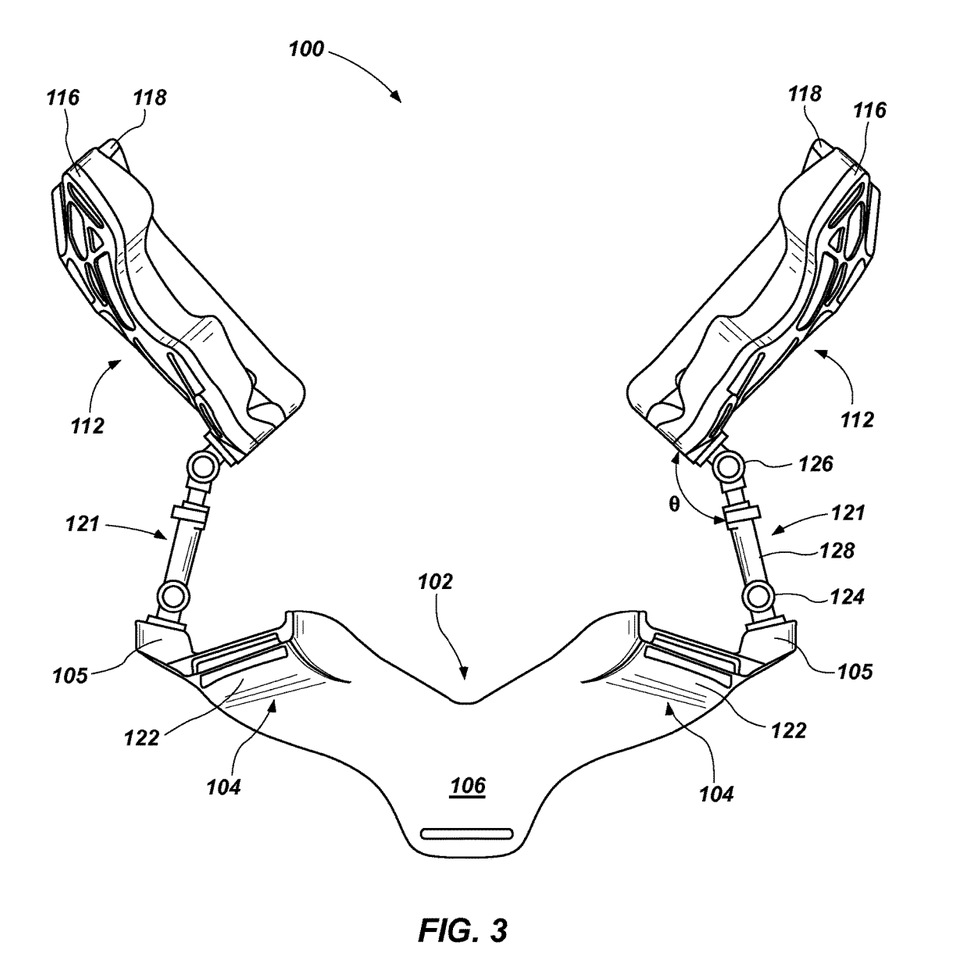
FIG. 3 is a front view of a portion of the head-and-neck immobilization device of FIG. 1.

FIG. 3 is a front view of a portion of the head-and-neck immobilization device 100 of FIG. 1 in a first state. In the first state, the head immobilization pads 112 may be spaced laterally from (i.e., may not be in contact with) the person's head even when the yoke 102 is in contact with the person's upper back and shoulders. The head immobilization pads 112 may then be rotated and extended relative to the yoke 102 utilizing the selectively rotatable, selectively rigid connections 121 to bring them into a second state in which they are in contact with the person's head (see FIG. 6) and secured in place to immobilize the person's neck and head.

A range of rotation θ of the first and second hinges 124 and 126 may be, for example, at least about 45°. More specifically, the range of rotation θ of the first and second hinges 124 and 126 may be, for example, at least about 90°. As specific, nonlimiting examples, the range of rotation θ of the first and second hinges 124 and 126 may be at least about 120°, at least about 180°, or more.

Figure 4:
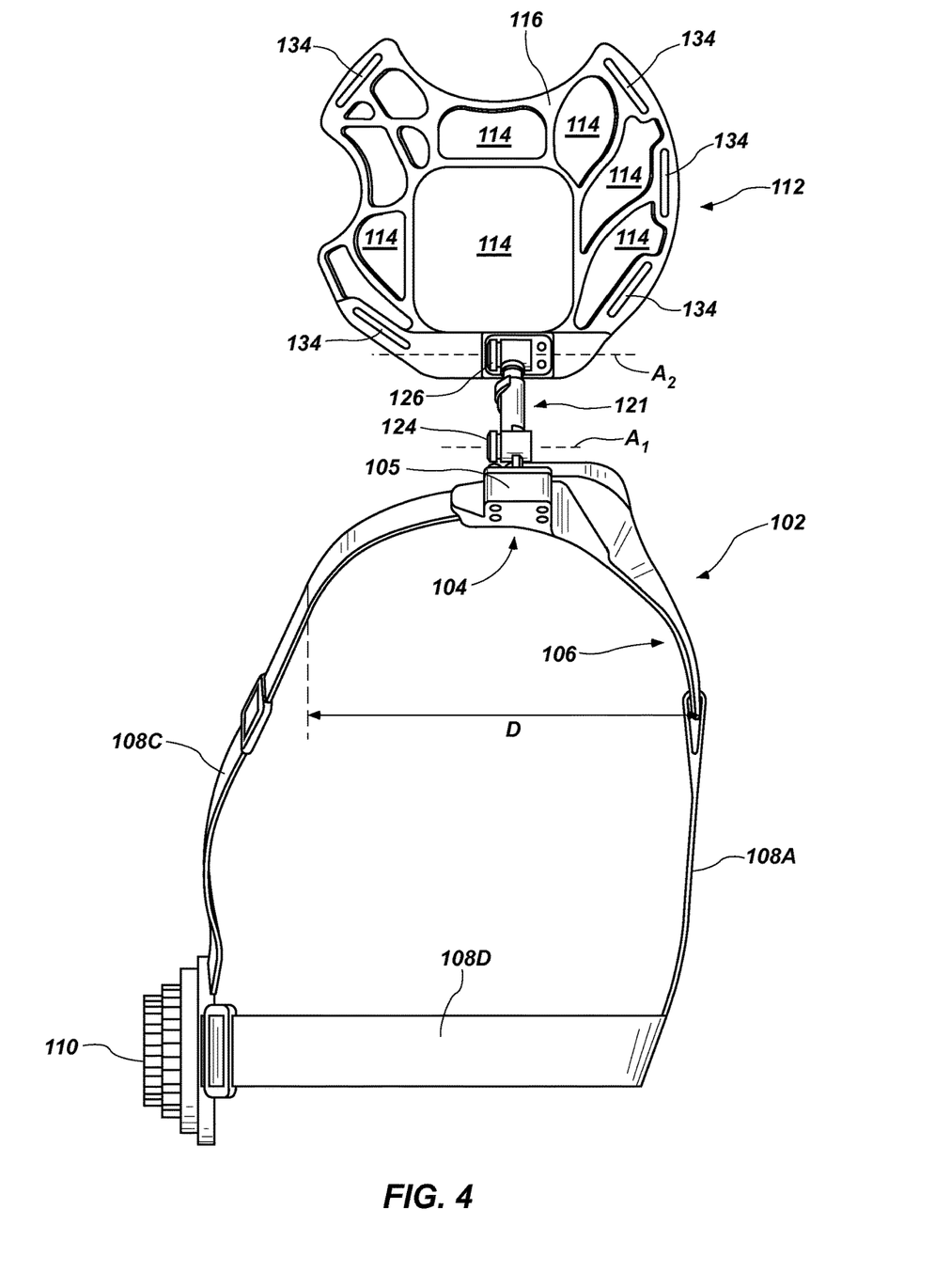
FIG. 4 is a side view of the head-and-neck immobilization device of FIG. 1.

FIG. 4 is a side view of the head-and-neck immobilization device 100 of FIG. 1. An area of the footprint of the head immobilization pads 112 occupied by the access holes 114 may be greater than an area of the footprint of the head immobilization pads 112 occupied by the outer shell 116. For example, the area of the footprint of the head immobilization pads 112 occupied by the access holes 114 may be at least about 60% of the area of the footprint of the head immobilization pads 112. More specifically, the area of the footprint of the head immobilization pads 112 occupied by the access holes 114 may be, for example, at least about 70% of the area of the footprint of the head immobilization pads 112. As specific, nonlimiting examples, the area of the footprint of the head immobilization pads 112 occupied by the access holes 114 may be, for example, at least about 75%, at least about 80%, or at least about 85% of the area of the footprint of the head immobilization pads 112.

The head immobilization pads 112 may include optional, selectable strap attachment structures 134 configured to directly secure the head immobilization pads 112 to one another by straps. The selectable strap attachment structures 134 may be, for example, slots, holes, hooks, hook-and-pile attachments, or other structures for securing a band of material (e.g., webbing) to the respective head immobilization pad 112. The selectable strap attachment structures 134 may be distributed about a periphery of the respective head immobilization pad 112 to enable someone placing the head-and-neck immobilization device 100 on another person to use those selectable strap attachment structures 134 easiest to access, most secure for the other person's head, or that will not result in obstruction of an injury for attachment of a strap when straps are located in the strap attachment structures 134.

Axes of rotation $A_1$ and $A_2$ of the first and second hinges 124 and 126 may extend at least substantially parallel to a transverse plane of the person's body (i.e., a plane dividing the body into superior and inferior, also known as upper and lower, parts) in some embodiments. Such an orientation for the first and second hinges 124 and 126 may enable rotation of the selectively rotatable, selectively rigid connections 121 to move the head immobilization pads 112 up and away from the person's head or down and toward the person's head.

In some embodiments, an overall depth D of the yoke 102 from chest to back of between about 4 in and about 8 in. For example, the depth D of the yoke 102 may be between about 5 in and about 7 in. As a specific, nonlimiting example, the depth D of the yoke 102 may be about 5.2 in.

Figure 5:
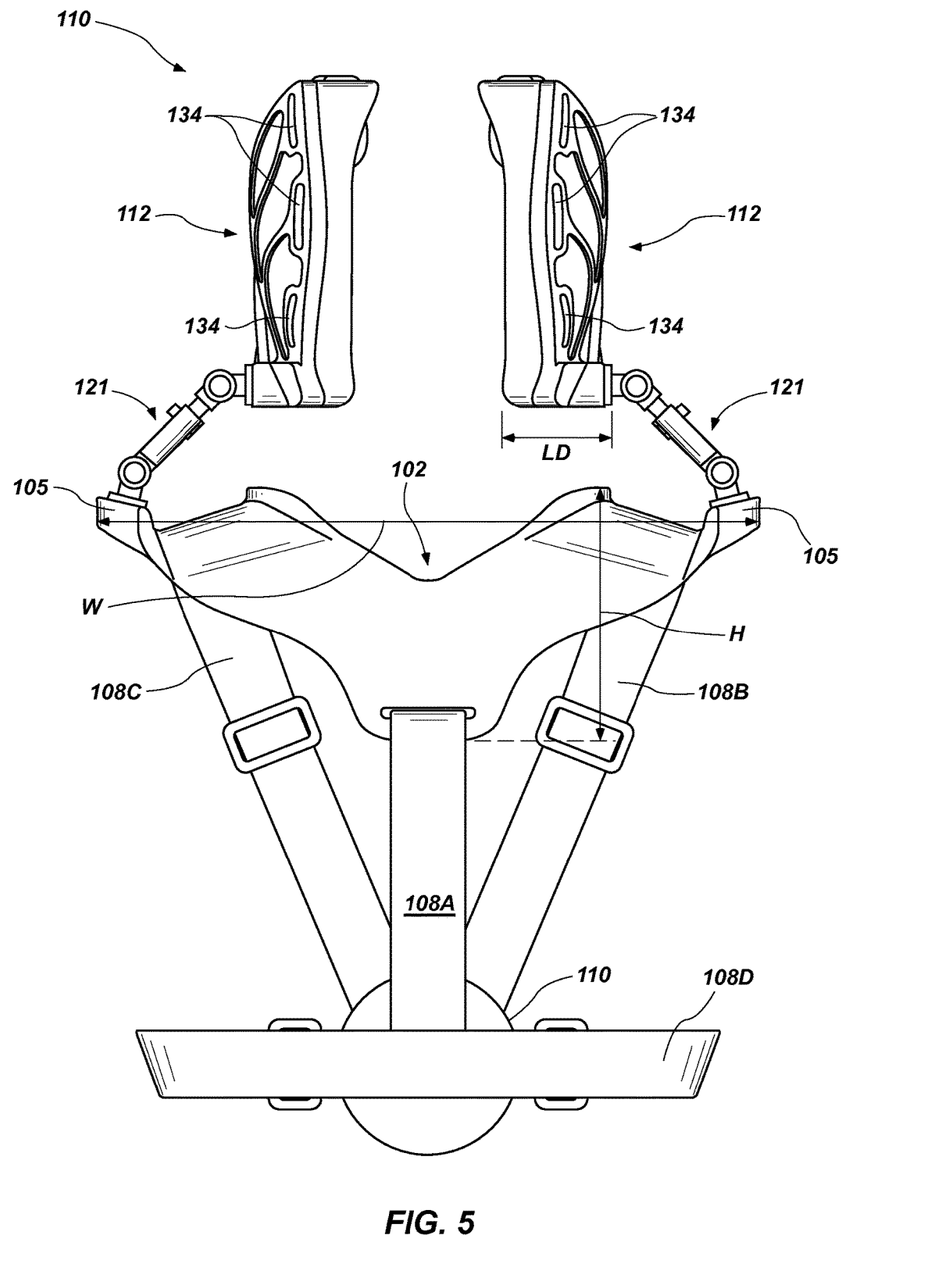
FIG. 5 is a rear view of the head-and-neck immobilization device of FIG. 1.

FIG. 5 is a rear view of the head-and-neck immobilization device 100 of FIG. 1. In some embodiments, the selectable strap attachment structures 134 may not be used when the head immobilization pads 112 are secured in place. In such embodiments, the head immobilization pads 112 may remain not directly secured to one another when the head immobilization pads 112 contact the two opposing sides of the person's head and are rigidly secured in place to immobilize the person's neck and head. For example, the only connection between the head immobilization pads 112 may be an indirect connection from the selectively rotatable, selectively rigid connections 121, through the yoke 102.

The head-and-neck immobilization device 100 may leave a greater proportion of the person's head and neck unobstructed when compared to conventional stabilization devices, reducing the risk of pressure ulcerations and increasing caregiver access to the person. For example, a majority of a posterior (i.e., a back) of the person's head may remain unobstructed by the head-and-neck immobilization device 100 (e.g., may not be covered by the head immobilization pads 112 and any straps extending between the head immobilization pads 112) when the two head immobilization pads 112 contact the two opposing sides of the person's head and are rigidly secured in place to immobilize the person's neck and head. In addition, a majority of a superior portion (i.e., a top) of the person's head may remain unobstructed by the head-and-neck immobilization device 100 when the two head immobilization pads 112 contact the two opposing sides of the person's head and are rigidly secured in place. For example, at least about 55% of a surface area of the posterior and superior portions of the person's head may remain unobstructed. More specifically, at least about 65% of a surface area of the posterior and superior portions of the person's head, for example, may remain unobstructed. As specific, nonlimiting examples, at least about 75%, at least about 80%, or more of a surface area of the posterior and superior portions of the person's head may remain unobstructed.

In some embodiments, the head-and-neck immobilization device 100 may not make contact with the person's neck when the two head immobilization pads 112 contact the two opposing sides of the person's head and are rigidly secured in place to immobilize the person's neck and head. For example, none of the head immobilization pads 112, the yoke 102, and the selectively rotatable, selectively rigid connections 121 may contact the person's neck. A lateral distance LD between the person's neck and the selectively rotatable, selectively rigid connections 121 as measured from the person's neck, along a transverse plane intersecting the person's larynx, to a respective selectively rotatable, selectively rigid connection 121, may be, for example, at least about 1 in. More specifically, the lateral distance LD (see also FIG. 9) between the person's neck and the selectively rotatable, selectively rigid connections 121 may be, for example, at least about 2 in. As specific, nonlimiting examples, the lateral distance LD between the person's neck and the selectively rotatable, selectively rigid connections 121 may be, for example, at least about 3 in, at least about 4 in, or more. In other embodiments, one or more components of the head-and-neck immobilization device 100, such as, for example, one or more straps extending between the head immobilization pads 112, may contact the person's neck.

In some embodiments, such as that shown in FIG. 5, the yoke 102 may be sized and shaped not to extend to the person's lower back. For example, a lowermost extent of the yoke 102 may be located at the proximate the person's upper back, between the person's shoulder blades, or at the person's middle back when the yoke 102 is secured in place by the straps 108 and the yoke 102 contacts the person's shoulders. A total height H of the yoke 102 as measured in a vertical direction parallel to the person's sagittal plane (i.e., a plane dividing the body into right and left halves) may be, for example, about 18 in or less. More specifically, the total height H of the yoke 102 may be, for example, about 12 in or less. As a specific, nonlimiting example, the total height H of the yoke 102 may be about 6 in or less. In some embodiments, the yoke 102 may have an overall width W as measured from left to right of between about 10 in and about 18 in. For example, the yoke 102 may have a width W of between about 12 in and about 16 in. As a specific, nonlimiting example, the yoke 102 may have a width W of about 14.5 in.

Figure 6:
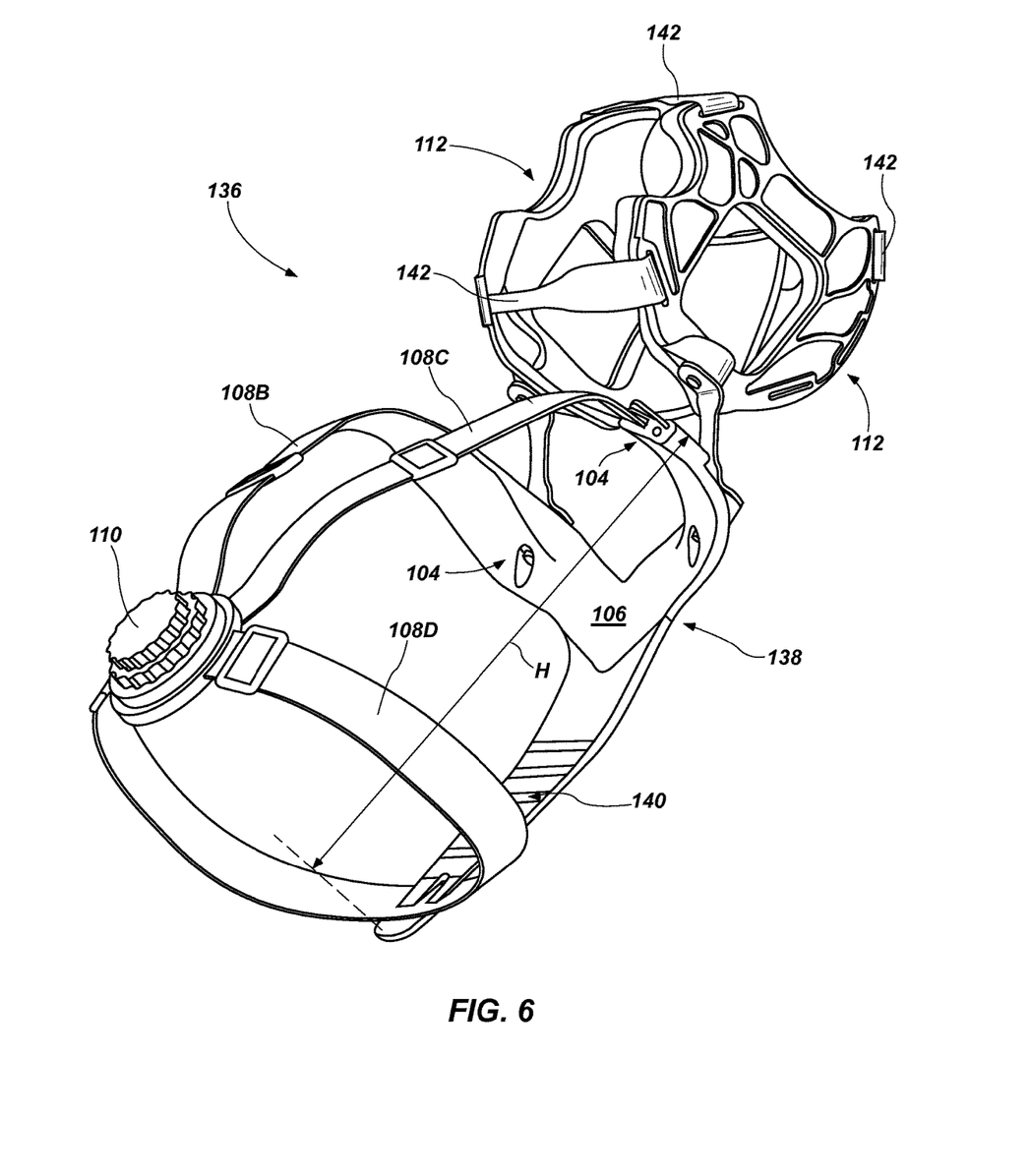
FIG. 6 is a perspective view of another embodiment of a head-and-neck immobilization device.

FIG. 6 is a perspective view of another embodiment of a head-and-neck immobilization device 136. The head-and-neck immobilization device 136 may be configured at least substantially similarly to the head-and-neck immobilization device 100 of FIG. 1, with differences described as follows. In some embodiments, such as that shown in FIG. 6, the yoke 138 may be sized and shaped to extend downwardly beyond the person's upper back. For example, a lowermost extent of the yoke 138 may be located at the person's lower back or at the person's waist when the yoke 138 is secured in place by the straps 108 and the yoke 138 contacts the person's shoulders. In such embodiments, the yoke 138 may include a lower back portion 140, which may be an extended strip of material depending from the upper back portion 106 and extending downward toward the person's waist. The lower back portion 140 may be flexible or rigid, and may take the place of the first strap 108A, such that the lower back portion 140 of the yoke 138 may be directly connected to the fourth strap 108D. In such embodiments, a total height H of the yoke 138 as measured in a vertical direction parallel to the person's sagittal plane (i.e., a plane dividing the body into right and left halves) may be, for example, about 20 in or more. More specifically, the total height H of the yoke 102 may be, for example, about 24 in or more. As a specific, nonlimiting example, the total height H of the yoke 102 may be about 26 in or more. In embodiments where the lower back portion 140 is flexible, its flexibility may only be parallel to the sagittal plane (i.e., moving towards front and back), and not perpendicular to the sagittal plane (i.e., not sideways).

In some embodiments, the selectable strap attachment structures 134 may be used in connection with headstraps 142 when the head immobilization pads 112 are secured in place. In such embodiments, the head immobilization pads 112 may be directly secured to one another by the headstraps 142 when the head immobilization pads 112 contact the two opposing sides of the person's head and are rigidly secured in place to immobilize the person's neck and head. For example, headstraps 142 may be used to secure fewer than all of the selectable strap attachment structures 134 of the head immobilization pads 112, such as, for example, one, two, three, or four of the selectable strap attachment structures 134, to one another. As another example, headstraps 142 may be used to secure all of the selectable strap attachment structures 134 to one another.

Figure 7:
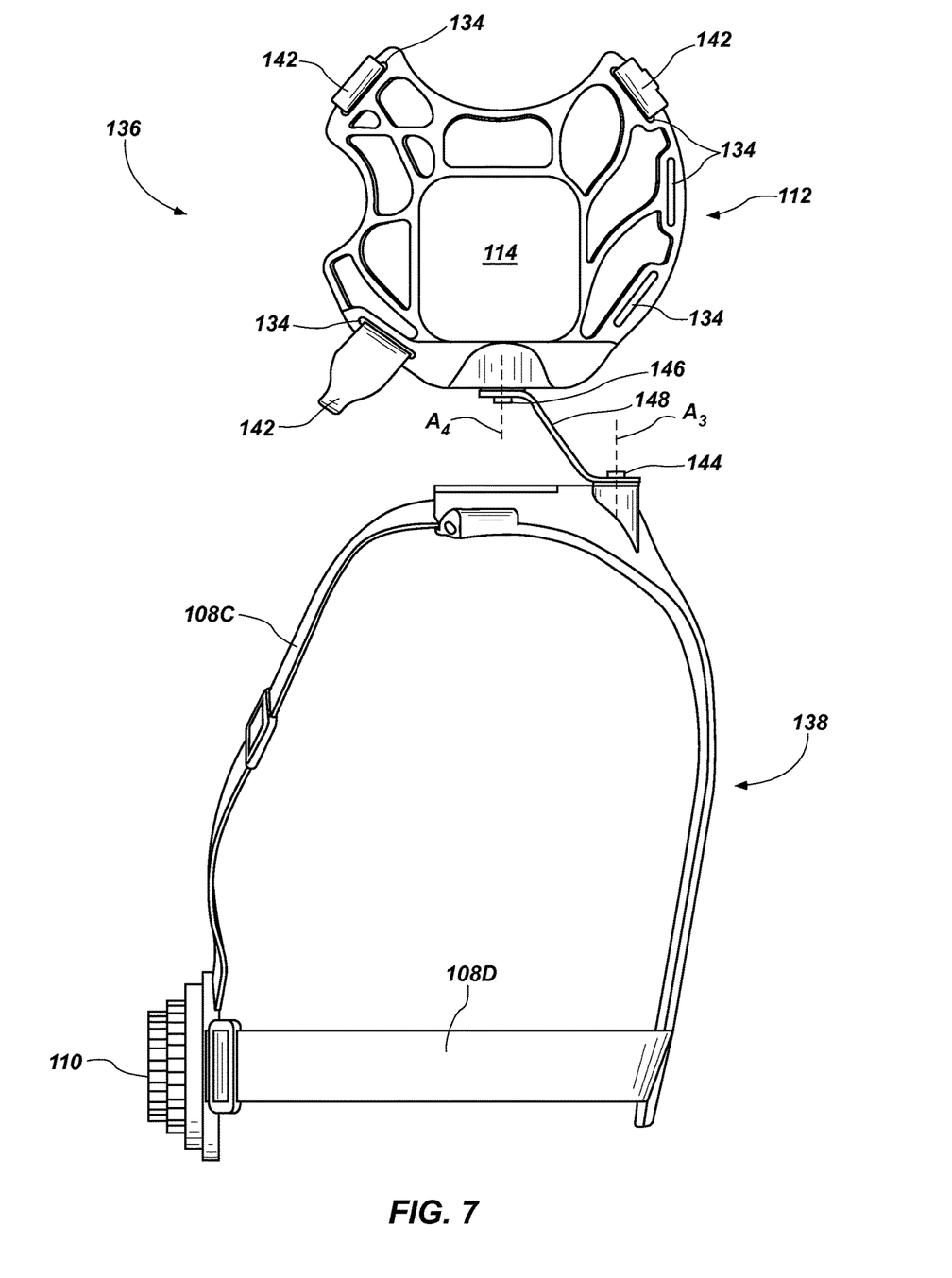
FIG. 7 is a side view of the head-and-neck immobilization device of FIG. 6.

FIG. 7 is a side view of the head-and-neck immobilization device 136 of FIG. 6. Axes of rotation $A_3$ and $A_4$ of the first and second hinges 144 and 146 may extend at least substantially parallel to the coronal plane of the person's body (i.e., a plane dividing the body into ventral and dorsal, also known as belly and back, sections) in some embodiments. Such and orientation for the first and second hinges 144 and 146 may cause rotation of the selectively rotatable, selectively rigid connections 148 to move the head immobilization pads 112 laterally distal, away from the person's head or laterally proximal, toward the person's head.

Figure 8:
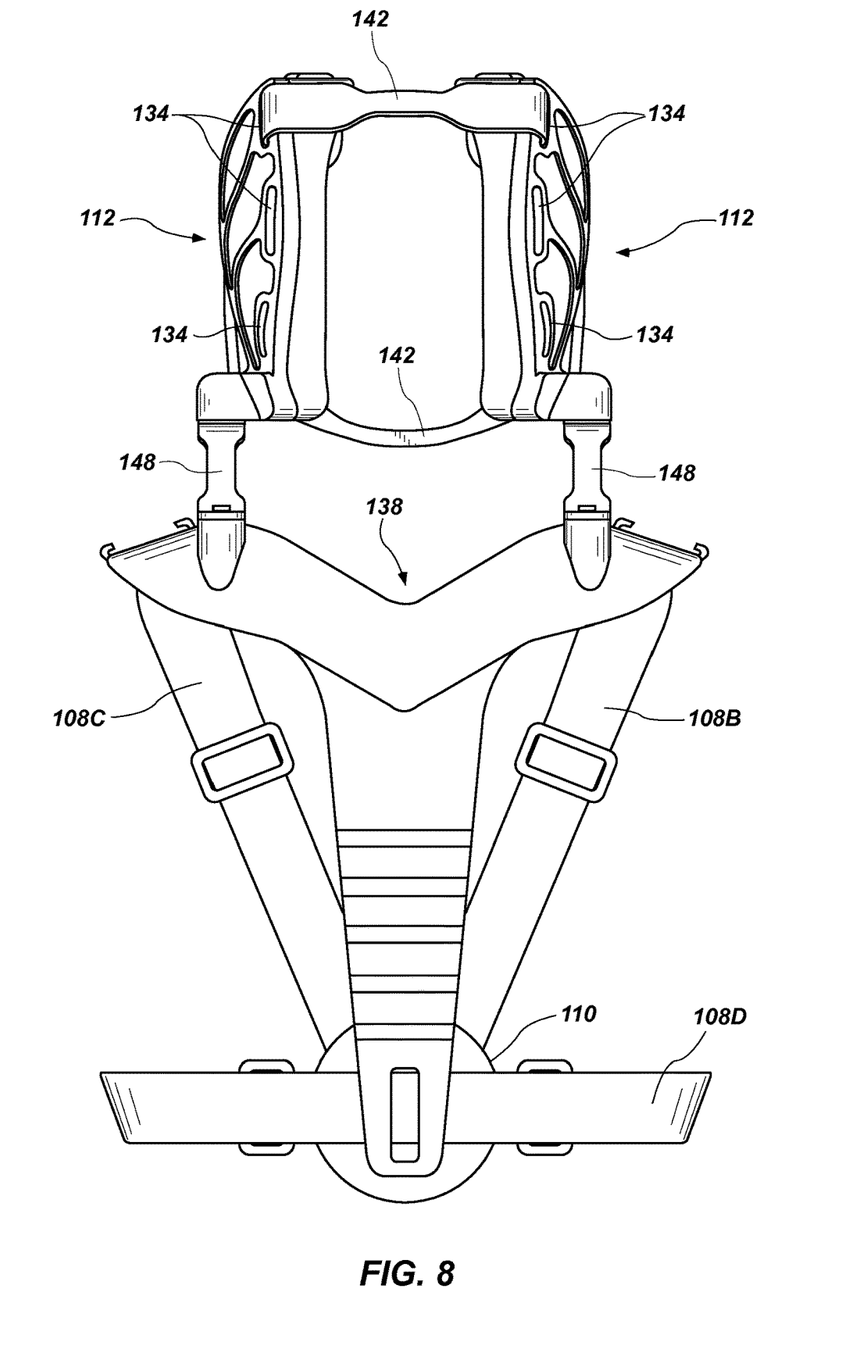
FIG. 8 is a rear view of the head-and-neck immobilization device of FIG. 6.

FIG. 8 is a rear view of the head-and-neck immobilization device of FIG. 7. Even with the headstraps 142 in place on multiple strap attachment structures 134, the head-and-neck immobilization device 136 may leave a greater proportion of the person's head and neck unobstructed when compared to conventional stabilization devices, reducing the risk of pressure ulcerations and increasing caregiver access to the person. For example, a majority of a posterior (i.e., a back) of the person's head may remain unobstructed by the head-and-neck immobilization device 136 (e.g., may not be covered by the head immobilization pads 112 and the headstraps 142 extending between the head immobilization pads 112) when the two head immobilization pads 112 contact the two opposing sides of the person's head and are rigidly secured in place to immobilize the person's neck and head. In addition, a majority of a superior portion (i.e., a top) of the person's head may remain unobstructed by the head-and-neck immobilization device 100 when the two head immobilization pads 112 contact the two opposing sides of the person's head and are rigidly secured in place. For example, at least about 51% of a surface area of the posterior and superior portions of the person's head may remain unobstructed. More specifically, at least about 60% of a surface area of the posterior and superior portions of the person's head, for example, may remain unobstructed. As specific, nonlimiting examples, at least about 65%, at least about 70%, or more of a surface area of the posterior and superior portions of the person's head may remain unobstructed.

Figure 9:
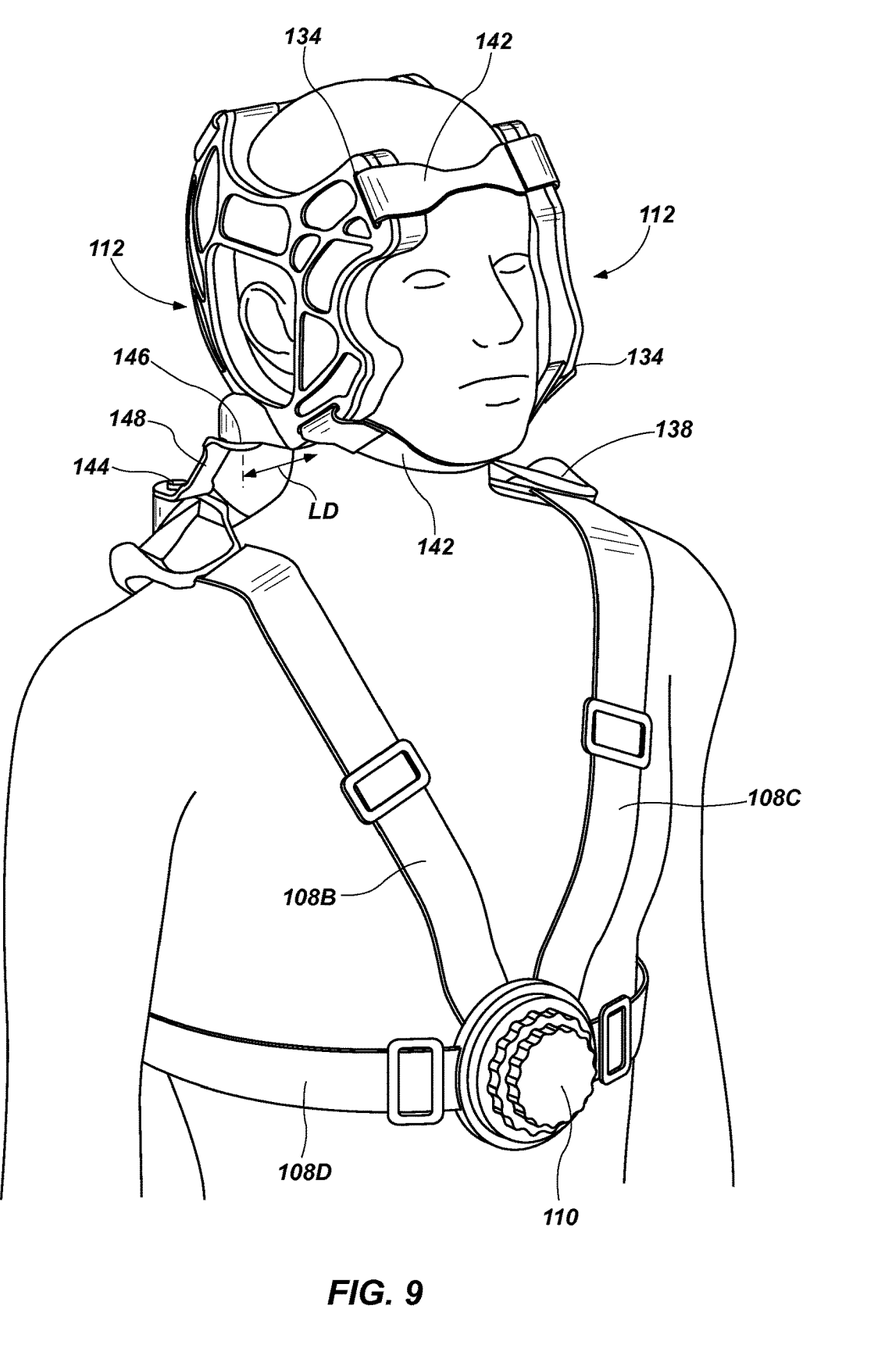
FIG. 9 is a perspective view of the head-and-neck immobilization device of FIG. 6 when secured on a representation of a person.

FIG. 9 is a perspective view of the head-and-neck immobilization device 136 of FIG. 6 when secured on a representation of a person. To position the head-and-neck immobilization device 136 (or 100, see FIG. 1) on a person, the yoke 102 may be brought into place by positioning it behind the person's head and pulling on the fourth strap 108D to slide the yoke past the person's head, behind the person's upper back, into contact with the person's shoulders. The yoke 138 (or 102, see FIG. 1) may be secured to the person's torso by attaching the second and third straps 108B and 108C to the buckle 110, securing the fourth strap 108D to the buckle 110, and adjusting the length of any straps 108 to ensure a snug fit on the person's torso. The yoke 138 (or 102, see FIG. 1) may be securable to the torso of the person when the person is in a variety of positions, reducing the need to reposition the person before applying the head-and-neck immobilization device, which may reduce the risk of further injuring the person.

The head immobilization pads may be brought into place by rendering the first and second hinges 144 and 146 (or 124 and 126, see FIG. 2) of the selectively rotatable, selectively rigid connections 148 (or 121, see FIG. 2) rotatable, such as, for example, by disengaging a quick-release mechanism, depressing a pin, or twisting a knob to disengage a locking mechanism of the selectively rotatable, selectively rigid connections 148 (or 121, see FIG. 2). The selectively rotatable, selectively rigid connections 148 (or 121, see FIG. 2) may be biased toward a locked, rigid state, such that releasing the locking mechanism may render the selectively rotatable, selectively rigid connections 148 (or 121, see FIG. 2) rigid. The head immobilization pads 112 may then be brought into place by rotating them relative to the yoke 138 (or 102, see FIG. 1) to bring the head immobilization pads 112 into contact with opposing lateral sides of the person's head. The selectively rotatable, selectively rigid connections 148 (or 121, see FIG. 2) may then be rendered rigid to immobilize the person's neck and head.

When the head immobilization pads 112 are in contact with the person's head and the selectively rotatable, selectively rigid connections 148 (or 121, see FIG. 2) are in a rigid state, the head-and-neck immobilization device 136 (or 100, see FIG. 1) may reduce the risk of further injury during transport and treatment. For example, the head-and-neck immobilization device 136 (or 100, see FIG. 1) may be configured to support a 95th percentile male head mass subjected to at least 3 g (i.e., three times the acceleration due to gravity of about 9.8 m/s$^2$) of acceleration in any direction that may be encountered in various types of transporting scenarios. More specifically, the head-and-neck immobilization device 136 (or 100, see FIG. 1) may be configured to support a 95th percentile adult male head mass subjected to, for example, at least 5 g of acceleration in any direction. As specific, nonlimiting examples, the head-and-neck immobilization device 136 (or 100, see FIG. 1) may be configured to support a 95th percentile adult male head mass subjected to at least 8 g, at least 10 g, or even greater acceleration in any direction.

When the selectively rotatable, selectively rigid connections 148 (or 121, see FIG. 2) are in a rigid state, the selectively rotatable, selectively rigid connections 148 (or 121, see FIG. 2) may be configured to support a torsional load of, for example, at least 240 inch-pounds. More specifically, the selectively rotatable, selectively rigid connections 148 (or 121, see FIG. 2) may be configured to support a torsional load of, for example, at least 400 inch-pounds. As specific, nonlimiting examples, the selectively rotatable, selectively rigid connections 148 (or 121, see FIG. 2) may be configured to support a torsional load of at least 500 inch-pounds, at least 600 inch-pounds, or even greater.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure will result in embodiments encompassed by the scope of this disclosure, such as those specifically claimed, including legal equivalents. In addition, features from one disclosed embodiment may be combined with features of another disclosed embodiment while still being within the scope of this disclosure, as contemplated by the inventors.

What is claimed is:

1. A head-and-neck immobilization device, comprising:
a yoke sized and shaped to contact back and shoulders of a person;
straps extending from the yoke, the straps located and configured to secure the yoke to the person's torso; and
two head immobilization pads sized and shaped to respectively contact opposing sides of the person's head, each of the two head immobilization pads connected to the yoke by a respective selectively rotatable, selectively fixed, connection;
wherein a majority of the person's head remains unobstructed by the head-and-neck immobilization device, and wherein the two head immobilization pads are secured to one another only indirectly from the selectively rotatable, selectively fixed connections through the yoke, when the two head immobilization pads contact the two opposing sides of the person's head and are rigidly secured in place to immobilize the person's neck and head.

2. The device of claim 1, wherein an axis of rotation of at least one of the selectively rotatable, selectively fixed connections extends at least substantially parallel to a coronal plane of the person's body.

3. The device of claim 1, wherein an axis of rotation of at least one of the selectively rotatable, selectively fixed, connections extends at least substantially parallel to a transverse plane of the person's body.

4. The device of claim 1, wherein an entirety of the person's neck remains unobstructed by the head-and-neck immobilization device when the two head immobilization pads contact the two opposing sides of the person's head and are rigidly secured in place to immobilize the person's neck and head.

5. The device of claim 1, wherein a majority of a posterior of the person's head remains unobstructed by the head-and-neck immobilization device when the two head immobilization pads respectively contact the opposing sides of the person's head and are rigidly secured in place to immobilize the person's neck and head.

6. The device of claim 1, wherein the head-and-neck immobilization device is configured to support a $95^{th}$ percentile adult male head mass subjected to up to 8 g of acceleration in any direction.

7. The device of claim 1, wherein each selectively rotatable, selectively fixed, connection is configured to support a torque of between 240 inch-pounds and 600 inch-pounds.

8. The device of claim 7, wherein each selectively rotatable, selectively fixed, connection is configured to support a torque of between 400 inch-pounds and 500 inch-pounds.

9. The device of claim 1, wherein each selectively rotatable, selectively fixed, connection extends from a respective shoulder portion of the yoke to a respective head immobilization pad of the two head immobilization pads.

10. The device of claim 9, wherein each selectively rotatable, selectively fixed, connection is selectively rotatable about at least two axes of rotation.

11. The device of claim 9, wherein each selectively rotatable, selectively fixed, connection is extensible.

12. A method of making a head-and-neck immobilization device, comprising:
sizing and shaping a yoke sized to contact a back and shoulders of a person;
securing straps to the yoke such that the straps extend from the yoke, the straps located and configured to secure the yoke to the person's torso;
connecting each of two head immobilization pads to the yoke by a selectively rotatable, selectively fixed, connection, the two head immobilization pads being sized and shaped to respectively contact opposing sides of the person's head; and
configuring each of the two head immobilization pads and each selectively rotatable, selectively fixed connection such that a majority of the person's head remains unobstructed by the head-and-neck immobilization device, and the two head immobilization pads are secured to one another only indirectly from the selectively rotatable, selectively fixed connections through the yoke, when the two head immobilization pads respectively contact the opposing sides of the person's head and are rigidly secured in place to immobilize the person's neck and head.

13. The method of claim 12, further comprising orienting an axis of rotation of at least one of the selectively rotatable, selectively fixed connections at least substantially parallel to a coronal plane of the person's body.

14. The method of claim 12, further comprising orienting an axis of rotation of at least one of the selectively rotatable, selectively fixed connections at least substantially parallel to a transverse plane of the person's body.

15. The method of claim 12, wherein the head-and-neck immobilization device is configured to support a $95^{th}$ percentile adult male head mass subjected to 8 g of acceleration in any direction.

16. The method of claim 12, wherein each selectively rotatable, selectively fixed, connection is configured to support a torque of between 240 inch-pounds and 600 inch-pounds.

17. A method of using a head-and-neck immobilization device, comprising:
contacting a yoke to a person's back and shoulders;
securing straps extending from the yoke around the person's torso to secure the yoke to the person's torso;
respectively contacting two head immobilization pads to opposing sides of the person's head, each of the two head immobilization pads connected to the yoke by a selectively rotatable, selectively fixed, connection, and rendering the selectively rotatable, selectively fixed, connection rigid to immobilize the person's head and neck; and
leaving a majority of the person's head unobstructed by the head-and-neck immobilization device, and leaving the two head immobilization pads secured to one another only indirectly from the selectively rotatable, selectively fixed connections through the yoke, when the two head immobilization pads contact the two opposing sides of the person's head and are rigidly secured in place to immobilize the person's neck and head.

* * * * *